US005756092A

United States Patent [19]
Michelet et al.

[11] Patent Number: 5,756,092
[45] Date of Patent: May 26, 1998

[54] USE, IN A COMPOSITION, AS CYCLOOXYGENASE ACTIVATOR AND/OR STABILIZER, OF AT LEAST ONE PYRIMIDINE DERIVATIVE SUSTITUTED AT THE 6TH POSITION AND A CYCLOOXYGENASE SUBSTRATE

[75] Inventors: Jean-François Michelet, Creteil; Yann Mahe, Morsang sur Orge; Bruno Bernard, Neuilly sur Seine, all of France

[73] Assignee: SociétéL'Oréal S.A., Paris, France

[21] Appl. No.: 628,473

[22] Filed: Apr. 5, 1996

[30] Foreign Application Priority Data

Apr. 5, 1995 [FR] France ................. 95 04049

[51] Int. Cl.$^6$ .............. A61K 38/44; C12N 9/96; C12N 9/02; A01N 43/54
[52] U.S. Cl. .............. 424/94.4; 435/188; 435/189; 514/269
[58] Field of Search ................. 424/94.3, 94.4; 435/188, 189, 192; 514/269, 861, 863, 846, 880

[56] References Cited

U.S. PATENT DOCUMENTS

| | | | |
|---|---|---|---|
| 4,973,474 | 11/1990 | Hocquaux | 424/70 |
| 5,356,898 | 10/1994 | Belliotti et al. | 514/269 |

FOREIGN PATENT DOCUMENTS

| | | |
|---|---|---|
| 0408442 | 1/1991 | European Pat. Off. . |
| 0459890 | 12/1991 | European Pat. Off. . |
| 0519819 | 12/1992 | European Pat. Off. . |
| 648488 | 9/1994 | France . |

OTHER PUBLICATIONS

J Lab Clin Med , Nov. 1989, 114 (5), pp. 575–578, U.S. O'Barr et al.

Biochem Pharmacol, Mar. 1, 1988, 37 (5), pp. 867–874, England, Kvedar et al.

Cancer Biochem Biophys, Oct. 1994, 14 (3), pp. 211–220, England, Billings et al.

Journal of Investigative Dermatology, 102 (4), 1994, 631, Grossman et al.

Primary Examiner—Jean C. Witz
Assistant Examiner—Susan Hanley
Attorney, Agent, or Firm—Burns, Doane, Swecker & Mathis, L.L.P.

[57] ABSTRACT

A composition and a method of treating alopecia or dermatological conditions with said composition are disclosed. The composition comprises at least one pyrimidine derivative substituted at the 6th position that activates and/or stabilizes cyclooxygenase, a pharmaceutically or cosmetically acceptable carrier and/or adjuvant and one of the following: a cyclooxygenase enzyme or a cyclooxygenase enzyme and at least one cyclooxygenase substrate comprising a polyunsaturated fatty acid having at least 20 carbon atoms. The composition is applied topically to the affected area or can be administered systemically.

24 Claims, No Drawings

USE, IN A COMPOSITION, AS CYCLOOXYGENASE ACTIVATOR AND/OR STABILIZER, OF AT LEAST ONE PYRIMIDINE DERIVATIVE SUSTITUTED AT THE 6TH POSITION AND A CYCLOOXYGENASE SUBSTRATE

BACKGROUND OF THE INVENTION

The invention relates to the use, in a composition, as cyclooxygenase activator and/or stabilizer, of at least one pyrimidine derivative substituted at the 6th position, to a kit and to a composition comprising at least one of these derivatives and to its use.

Cyclooxygenase should be understood to mean, in the present invention, any enzyme having a cyclooxygenase activity, it being possible for this enzyme to have other enzymatic activities.

The cyclooxygenase activity can be defined as the enzymatic activity which converts certain polyunsaturated fatty acids to cyclized oxygenated products which are in fact highly unstable endoperoxides which later enter subsequent metabolic pathways.

Prostaglandin-endoperoxide synthase (or PGHS, EC 1.14.99.1) which is a haemoprotein is one example of these enzymes which exhibit such an activity. It is involved in one of the metabolic pathways for the prostaglandins.

It is known that some polyunsaturated fatty acids, in particular those having 20 carbon atoms, such as arachidonic acid, dihomo-γ-linolenic acid or alternatively eicosapentaenoic acid, can be converted in vivo by the action of certain specific enzymes contained in living cells, to some other eicosanoid-type compounds present in the body. Thus, it is known that the enzymes termed cyclooxygenases generate, from the various fatty acids mentioned above, prostaglandin-type eicosanoids, and that the enzymes termed lipoxygenases are, for their part, responsible for the formation of leukotriene-type eicosanoids and other hydroxylated acyclic acids containing 20 carbon atoms.

The involvement of these enzymes in numerous metabolic pathways and thus the possible consequences of a deregulation of their function have led to numerous research studies being undertaken in order to identify substances having the capacity either to increase or to reduce the activity of these enzymes.

In the field of cyclooxygenase activators, the metabolites of arachidonic acid, nitrogen monoxide and nitrogen monoxide-donating compounds, stanozolol, glutathiondonating compounds, calcium ionophores, anthocyanosides, bioflavonoids, platelet activating factors (PAFs), proinflammatory cytokines, and bacterial endotoxins are known in particular.

Likewise, 6-chloro-2,3-dihydroxy-1,4-naphthoquinone (CNDQ) may be mentioned which has the characteristic of being both a lipoxygenase inhibitor and a cyclooxygenase stimulating agent (C. J. Bedford et al., The Journal of Investigative Dermatology, 81:566–571, 1983).

However, most of these substances have the major disadvantage of having a broad activity spectrum, which causes them not to have, in general, real specificity for cyclooxygenase. In this regard, the literature on this subject shows a wide range of interpretation. These substances may also be labile or their activity may depend on their concentration, which makes their use difficult.

The Applicant has therefore searched for new cyclooxygenase activators and/or stabilizers.

Surprisingly and unexpectedly, after long research studies, the Applicant has discovered that pyrimidine derivatives substituted at the 6th position, and more particularly the pyrimidine 3-oxide derivatives substituted at the 6th position, have the property of activating and/or stabilizing cyclooxygenase. This property suggests that cyclooxygenase is one of the receptors of pyrimidine derivatives substituted at the 6th position.

This discovery forms the basis of the present invention.

Thus, the subject of the invention is the use, in a composition, as cyclooxygenase activator and/or stabilizer, of at least one pyrimidine derivative substituted at the 6th position.

Advantageously, this derivative is a pyrimidine 3-oxide derivative substituted at the 6th position, in particular 2,4-diamino-6-piperidinopyrimidine 3-oxide or "Minoxidil".

The composition is more particularly a cosmetic or pharmaceutical composition.

Preferably, the pharmaceutical composition is a dermatological composition.

"Minoxidil" is known for its antihypertensive effects and for its capacity to promote hair growth. These properties are described in U.S. Pat. No. 4,596,812. Moreover, it is known of numerous other pyrimidine derivatives substituted at the 6th position. Among these, there may be mentioned especially those described in Patent Applications EP 353123, EP 356271, EP 408442, EP 522964, EP 420707, EP 459890, EP 519819.

Among the pyrimidine derivatives substituted at the 6th position which can be used according to the invention, there may be mentioned more particularly: 2,4-diamino-6-piperidinopyrimidine, 2,4-diamino-6-piperidinopyrimidine 3-oxide, 2,4-dipropylamino-6-dimethylaminopyrimidine 3-oxide, 2-amino-4-propylamino-6-piperidinopyrimidine 3-oxide, 2-methyl-4-amino-6-piperidinopyrimidine 3-oxide, 2,4-diamino-6-butyloxypyrimidine 3-oxide, 2-amino-4-propylamino-6-dimethylaminopyrimidine 3-oxide.

Preferably, the following are used according to the invention: 2,4-diamino-6-piperidinopyrimidine 3-oxide, 2,4-dipropylamino-6-dimethylaminopyrimidine 3-oxide, 2-amino-4-propylamino-6-piperidinopyrimidine 3-oxide, 2-methyl-4-amino-6-piperidinopyrimidine 3-oxide, 2,4-diamino-6-butyloxypyrimidine 3-oxide, 2-amino-4-propylamino-6-dimethylaminopyrimidine 3-oxide.

And still more preferably, the following are used according to the invention: 2,4-diamino-6-piperidinopyrimidine 3-oxide, 2,4-dipropylamino-6-dimethylaminopyrimidine 3-oxide, 2-amino-4-propylamino-6-piperidinopyrimidine 3-oxide.

The quantities necessary to activate and/or stabilize a cyclooxygenase of course depend on the nature of the pyrimidine derivative substituted at the 6th position and on the nature of the cyclooxygenase in question. In general, this concentration is greater than or equal to 1 nM, and preferably greater than 1 μM.

In order to determine the activity of the pyrimidine derivatives substituted at the 6th position, the Applicant used a simple and rapid measuring process consisting in incubating, in a suitable medium, an optionally purified cyclooxygenase and one of its substrates, in the presence of a compound to be tested, and in comparing the measurements obtained with the results of identical measurements taken during the incubation of the optionally purified cyclooxygenase with one of its substrates in the absence of the compound to be tested.

As indicated above, the enzymatic activity of a cyclooxygenase is indicated by a consumption of oxygen. It is therefore possible to monitor the course of the reaction in progress by measuring the consumption of oxygen in the reaction medium and thus to evaluate the activity of the enzyme by measuring the consumption of oxygen.

Indeed, it can be easily understood that the reaction involving on the part of the cyclooxygenase the use of oxygen molecules, the increase or the reduction in this consumption are a reflection of the variation of the activity of the enzyme.

Any known method of measuring the consumption of oxygen can of course be used in the process (see for example Vanderkooi J. M. and Wilson D. F. (1986) "A new method for measuring oxygen in biological systems" Adv. Exptl. Med. Biol. 200: 189–193).

In order to be able to evaluate rapidly the activating and/or stabilizing properties of the pyrimidine derivatives substituted at the 6th position, the Applicant used a method for the direct and continuous measurement of the consumption of oxygen with the aid of a Clark electrode (CLARK. L. C., Jr. (1956) Trans. Am. Soc. Artificial Internal Organs, 2.41.), coupled to a recording system.

Any recording system allowing automatic or nonautomatic calculation of the initial rate of the reaction and the period during which this initial rate is maintained may be used in this process.

The general procedure for the measurement can be summarized thus:

At time T=0 of the process, a buffered solution containing a cyclooxygenase is introduced into a measuring tank and then the whole is allowed to stabilize for at least one minute.

At time T=1 minute, an appropriate quantity of enzyme substrate is added and the oxygen consumption of the reaction is recorded.

This recording makes it possible to deduce the initial rate of the reaction and the period during which the initial rate of the reaction is maintained.

In the absence of any substance other than the ingredients necessary for the enzymatic reaction, it is thus possible to deduce the basic activity of the enzyme.

This data will serve as reference for studying the substances to be tested.

When a substance potentially having an activity on the cyclooxygenase is tested, the variation of the slope in a positive or negative direction relative to the results obtained with the enzyme alone reflects either the activation or the inhibition of the activity of the enzyme.

Thus, knowing that cyclooxygenase has the characteristic of being self-activating (W. Smith and L. Marnett, Biochim. Biophy. Acta, 1083 (1991) 1–17), a variation in the period during which the initial rate of the reaction is maintained at its maximum indicates a stabilization or a destabilization of the enzyme.

Cyclooxygenase is involved in numerous metabolic pathways. There may be mentioned, inter alia, as illustration the role played by this enzyme in the metabolism of prostaglandins.

It is also known that the same substrate, a polyunsaturated fatty acid for example, can be used by cyclooxygenase and by other metabolic enzymes. Competitive situations are in this case generally created between enzymes with respect to the same substrate. Often, this leads to radically opposed consequences.

In the case of polyunsaturated fatty acids, depending on the nature of the enzyme with which they would have first reacted, the formation of several different metabolites is obtained. For example, with arachidonic acid as substrate, cyclooxygenase and 5-lipoxygenase lead respectively to prostaglandins and to the precursors of leukotrienes.

Therefore, in some cases, starting with the same substrate, the choice of any particular enzyme, or the favouring of a particular metabolic pathway, for example by increasing the activity of any particular enzyme and/or by stabilizing it, will have the effect of not only favouring a particular metabolic pathway, but also of disfavouring the opposite metabolic pathway.

This is what happens when arachidonic acid is the substrate for cyclooxygenases and lipoxygenases (see for example Bedord C. J. et al., J. I. D. 81:566–571, 1983, or Williams K. L in "Nonsteroidal Anti-Inflammatory Drugs", Pharmacol. Skin. 2: 103–117, 1989, Karger editor).

Thus, the use of cyclooxygenase activators and/or stabilizers can favour the metabolic pathway for which this enzyme is involved at the expense of the opposite pathway, that is to say that for lipoxygenases.

Insofar as, in certain pathologies, it is recognized that the lipoxygenase pathway is abnormally activated, it becomes advantageous to be able to seek to correct this situation by seeking to increase the activity of cyclooxygenase in order to reduce, through competition, the activity of the lipoxygenase.

Thus, the subject of the invention is also the use of at least one pyrimidine derivative substituted at the 6th position, and more particularly a pyrimidine 3-oxide derivative substituted at the 6th position, as cyclooxygenase activator and/or stabilizer, in the preparation of a pharmaceutical composition intended for the treatment of pathologies linked either to hyperactivity of the lipoxygenase pathway or simply to a deficiency in the activity of the cyclooxygenase pathway, or alternatively for which it is found to be useful to favour the cyclooxygenase pathway in order to initiate and/or accelerate a process.

Preferably, the pyrimidine 3-oxide derivative substituted at the 6th position used in this preparation is 2,4-diamino-6-piperidinopyrimidine 3-oxide.

In this regard, there may be mentioned the treatment of dermatological conditions such as, inter alia and with no limitation being implied, solar erythema, pruritus, eczema, psoriasis, erythema nodosum, urticaria and systemic mastocytosis (de Lacharrière O. et al., "Nonsteroidal anti-inflammatory agents and the skin", Thérapeutique Dermatologique, L. Dubertret editor, Flammarion-Médecine-Sciences Paris, 1991, pp: 698–707).

There may also be mentioned the use in the preparation of a pharmaceutical composition intended to promote haemostasis for the treatment of wounds or of epistaxis or in the preparation of an anti-ageing composition.

The pharmaceutical composition can be used via the local route or via the systemic route.

Via the systemic route, there may be mentioned the parenteral route or preferably the enteral route, or particularly the oral route.

The composition may also be a cosmetic composition, generally used via the local route.

Via the local route, the topical route is preferred, that is to say by direct application to the skin, the scalp, the nails or the mucous membranes.

Regardless of the form of the composition, it may comprise, in addition, any compound normally used in cosmetics and/or in pharmacy.

The composition according to the invention is a physiologically acceptable composition. It may be anhydrous or, on the contrary, aqueous. When it is anhydrous, it contains less than 1% of water. It may consist of a solvent or a mixture of solvents chosen more particularly from $C_2$–$C_4$ lower alcohols such as ethyl alcohol, alkylene glycols such as propylene glycol, and alkyl ethers of alkylene glycols or of dialkylene glycols, whose alkyl or alkylene radicals contain from 1 to 4 carbon atoms. When it is aqueous, it consists of water or a mixture of water and another physiologically acceptable solvent chosen especially from the organic solvents mentioned above. In the latter case, these other solvents, when they are present, represent about 5 to 95% by weight of the composition.

The composition may contain other adjuvants normally used in the cosmetic or pharmaceutical field, such as surface-active agents, emulsifying agents, thickening or gelling agents, oils, preservatives, alkalinizing or acidifying agents which are well known in the prior state of the art, hydrophilic or lipophilic gelling agents, hydrophilic or lipophilic active agents, preservatives, antioxidants, solvents, perfumes, fillers, screening agents, bactericides, odour absorbers and colouring matter.

The quantities used are sufficient to obtain the desired form of presentation, especially a lotion which is thickened to a greater or lesser degree, a gel, an emulsion or a cream. The composition can optionally also be pressurized as an aerosol or sprayed from a pump dispenser.

The quantities of these various adjuvants are those conventionally used in the cosmetic or pharmaceutical field, and for example are from 0.01% to 90% of the total weight of the composition. These adjuvants, depending on their nature, can be introduced into a fatty phase, into an aqueous phase and/or into lipid spherules.

As oils which can be used in the invention, there may be mentioned mineral oils (liquid paraffin), vegetable oils (liquid fraction of shea butter, sunflower oil), animal oils (perhydrosqualene), synthetic oils (Purcellin oil), silicone oils (cyclomethicone) and fluorinated oils (perfluoropolyethers). It is also possible to use, as fatty substances, fatty alcohols, fatty acids (stearic acid) and waxes (paraffin, carnauba or beeswax).

As emulsifiers which can be used in the invention, there may be mentioned for example glyceryl stearate, polysorbate 60 and the PEG-6/PEG-32/glycol stearate mixture sold under the name Tefose® 63 by the company Gattefosse.

As solvents which can be used in the invention, there may be mentioned lower alcohols, especially ethanol and isopropanol, and propylene glycol.

As hydrophilic gelling agents, there may be mentioned carboxyvinyl polymers (carbomer), acrylic copolymers such as acrylate/alkylacrylate copolymers, polyacrylamides, polysaccharides such as hydroxypropyl cellulose, natural gums and clays, and, as lipophilic gelling agents, there may be mentioned modified clays such as bentones, metal salts of fatty acids such as aluminium stearates and hydrophobic silica, or alternatively ethyl cellulose and polyethylene.

As hydrophilic active agents, proteins, protein hydrolysates, amino acids, polyols, urea, allantoin, sugars and sugar derivatives, water-soluble vitamins, starch and plant extracts, such as those of Aloe vera may be used.

As lipophilic active agents, retinol (vitamin A) and its derivatives, tocopherol (vitamin E) and its derivatives, essential fatty acids, polyunsaturated fatty acids, ceramides and essential oils may be used.

The composition may contain, in addition, enzymes, such as in particular a cyclooxygenase. This cyclooxygenase is purified or is produced by genetic engineering, or is of animal or plant origin.

Such compositions are particularly suitable for the treatment of alopecia.

The term alopecia covers a range of categories of impairments of the hair follicle, the final consequence of which is the partial or general permanent loss of the hair.

The composition is more particularly a cosmetic or pharmaceutical composition.

Preferably, the pharmaceutical composition is a dermatological composition.

The activating and/or stabilizing properties of the pyrimidine derivatives substituted at the 6th position are equally advantageous because of the high cost of cyclooxygenase, in particular when it is in purified form. Thus, the addition to the enzyme of at least one of these derivatives can make it possible, because of the activation and/or stabilization which it generates, to reduce the quantity of enzyme used.

In this regard, the invention also relates to a kit comprising at least one cyclooxygenase, optionally in a purified form, and at least one activator and/or stabilizer thereof. This activator and/or stabilizer is a pyrimidine derivative substituted at the 6th position and in particular a pyrimidine 3-oxide derivative substituted at the 6th position. Preferably, this pyrimidine 3-oxide derivative substituted at the 6th position is 2,4-diamino-6-piperidinopyrimidine 3-oxide.

The compounds of this kit can optionally be packaged separately.

These kits are also particularly suitable for the treatment of alopecia.

The invention relates more specifically to a kit comprising, in addition, at least one of the cyclooxygenase substrates.

Such a kit may be used, for example, to determine the cyclooxygenase-inhibiting effects of a substance which may be active.

In some cases, it may prove necessary to increase the activity of the endogenous cyclooxygenases.

Thus, the subject of the present invention is also a composition containing at least one cyclooxygenase substrate and at least one pyrimidine derivative substituted at the 6th position and more particularly a pyrimidine 3-oxide derivative substituted at the 6th position. Preferably, this derivative is 2,4-diamino-6-piperidinopyrimidine 3-oxide.

In this case, the derivative used may come to activate and/or stabilize a cyclooxygenase present in any tissue, and more particularly in the skin.

Such a composition may be administered enterally, parenterally, but preferably topically.

Preferably, the cyclooxygenase substrate is a polyunsaturated fatty acid and still more preferably arachidonic acid.

This composition may comprise, in addition, at least cyclooxygenase. The latter composition finds several applications in a wide variety of fields such as cosmetics, pharmacy or alternatively the agrifood industry. It is found to be highly advantageous as oxygen scavenger.

Indeed, during the reaction between the cyclooxygenase and its substrate, there is consumption of oxygen. This consumption of oxygen may be increased by adding to the mixture at least one cyclooxygenase activator and/or stabilizer. It is therefore possible to use a composition of this type in order to remove the oxygen from a medium so as to protect the latter from oxidation.

The subject of the invention is also the use, as oxygen scavenger, of a composition comprising at least one cyclooxygenase, at least one of its substrates and at least one pyrimidine derivative substituted at the 6th position and more particularly one pyrimidine 3-oxide derivative substituted at the 6th position. Preferably, this derivative is 2,4-diamino-6-piperidinopyrimidine 3-oxide.

In some specific uses of such a scavenger, it may be necessary to be able to isolate it from its medium. This is especially the case when the scavenger described above is used in sectors such as the agrifood industry or cosmetics. It is indeed necessary to remember that the enzymatic reaction which constitutes the central component of the scavenger leads to the formation of compounds which it may be necessary not to mix with the object to be protected from oxygen.

A specific packaging should, in this case, be provided which makes it possible to physically isolate the oxygen scavenger thus defined from the medium to be protected from oxygen. In one specific embodiment of the invention, the oxygen scavenger is isolated from the product contained in the packaging by a membrane permeable to gas and impermeable to liquids, especially those entering into the composition of the emulsion according to the invention.

The gas-permeable membrane may be, for example, that defined in the document FR-A-2,671,055.

The oxygen scavenger isolated by the membrane may be, in the packaging device, integrally attached to the walls or not integrally attached to these walls and embedded in the composition.

Regardless of the composition envisaged according to the invention, persons skilled in the art know how to adjust the concentration of the various components therein, knowing that the basal activity of the enzyme can vary unpredictably depending on the batch used and that this activity determines the quantities of substrate and/or activator and/or stabilizer used.

Examples will now be given, by way of illustration, of measurements of cyclooxygenase activity in the presence or in the absence of derivatives and in particular of pyrimidine derivatives, which do not in any manner limit the scope of the invention.

EXAMPLE 1

Measurement of the activating and/or stabilizing power of pyrimidine derivatives substituted at the 6th position, at a given concentration.

General principles of the measurement:

The quantity of oxygen necessary for the oxidation of arachidonic acid is measured by the cyclooxygenase activity of prostaglandin-endoperoxide synthase, in the presence or absence of the derivative to be tested.

The measurements of the consumption of oxygen are performed with a Clark electrode connected to a YSI 5300 oxygen meter of the Yellow Spring Instruments trademark.

These measurements are performed in an open chamber, with constant stirring, at a temperature of 37° C.

If a graph recorder is used, the measurement of the oxygen consumption takes the form of a curve whose maximum slope makes it possible to deduce the initial rate of the reaction, and from which it is possible to calculate the period during which the initial rate of the reaction is maintained.

The curve thus obtained, in the absence of any substance other than the ingredients necessary for the enzymatic reaction, gives the basic activity of the enzyme. It is possible to determine, under these conditions, the initial rate and the period during which this rate is maintained, in a reaction containing only the enzyme and its substrate.

This data will serve as reference for studying the derivatives to be tested.

The measurement of the activity of the derivatives to be tested is performed under the same conditions, by adding, to the reaction medium, the derivative to be tested. It is the variation of the slope and the variation of the period during which the maximum rate is maintained which make it possible to evaluate the activity of the derivative to be tested towards cyclooxygenase.

Preparation for the measurements:

A solution of 0.1M TRIS and 5 mM EDTA at pH=8.00 (TE solution) is prepared.

The measurements are performed in a buffered solution (TEA buffer) composed of 9 volumes of TE solution and 1 volume of 20% alcohol.

The substrate is prepared in the form of a stock solution of potassium arachidonate according to the manufacturer's procedure (Interchim, France).

The solution thus obtained has an arachidonic acid titre of 46 mM. It can be stored at 4° C. for 24 hours.

The enzyme used is prostaglandin-endoperoxide synthase (PGHS), isolated from sheep seminal gland, sold by the company Cayman Chemical under the reference 60100.

The derivatives to be tested are prepared in the form of a stock solution with a titre of 5 mM in a water/alcohol mixture (80/20) and tested with the same batch of enzyme.

Measurements:

Basic activities of the enzyme:

At t=0, there are introduced into the measuring chamber 380 µl of TEA buffer preheated to 37° C. that are allowed to equilibrate for at least one minute.

At t=1, 300 units of enzyme (PGHS) are introduced.

The recording is initiated and the whole is again allowed to stabilize for one minute. The recording obtained gives the base level of the reaction.

After an additional minute, 10 µl of substrate are introduced and the consumption of oxygen is recorded for 2 to 3 minutes.

The initial rate of the reaction and the period during which this rate is maintained are thus determined.

These data will serve as reference for the measurements of the activity of the derivatives to be tested.

Activities of the derivatives to be tested:

The experimental conditions are identical to those above, except that the TEA buffer preheated to 37° C. is replaced by an identical buffer containing the derivative to be tested at a concentration of 0.5 mM.

Results:

These results are expressed in % relative to the values obtained with the control.

| Derivatives | Activation | Stabilization |
|---|---|---|
| Control | +0% | +0% |
| 2,4-diamino-6-piperidinopyrimidine 3-oxide | +58% | +14% |
| 2,4-diamino-6-piperidinopyrimidine | −14% | +35% |
| 2,4-dipropylamino-6-dimethylaminopyrimidine 3-oxide | +171% | +28% |
| 2-amino-4-propylamino-6-piperidinopyrimidine 3-oxide | +173% | +17% |

9

-continued

| Derivatives | Activation | Stabilization |
|---|---|---|
| 2-methyl-4-amino-6-piperidinopyrimidine 3-oxide | +24% | 0% |
| 2,4-diamino-6-butyloxypyrimidine 3-oxide | +13% | 0% |
| 2-amino-4-propylamino-6-dimethylamino-pyrimidine 3-oxide | +117% | 0% |
| Indomethacin[1] | −100% | −100% |

[1] 1-(4-Chlorobenzoyl)-5-methoxy-2-methyl-1H-indole-3-acetic acid or indomethacin is a known inhibitor of cyclooxygenase activity (H. P. Range/ M. M. Dale Pharmacology second edition 1991. Churchill Livingstone edition). Under the experimental conditions this inhibitory effect is indeed observed.

These results show that pyrimidine derivatives substituted at the 6th position possess cyclooxygenase activating and/or stabilizing properties.

EXAMPLE 2

Calculation of the 50% activating concentration (AC 50) of 2,4-diamino-6-piperidinopyrimidine 3-oxide for the activation of prostaglandin-endoperoxide synthase. 2,4-diamino-6-piperidinopyrimidine 3-oxide Activation

| 2,4-diamino-6-piperidinopyrimidine 3-oxide (µM) | Activation (% of control) |
|---|---|
| 0 | 0 |
| 15.6 | 23 |
| 62.5 | 61 |
| 125 | 90 |
| 250 | 102 |
| 500 | 146 |
| 1000 | 181 |

By a statistical calculation (log-linear regression, the correlation coefficient being 0.98 and the significance of the binding less than or equal to 0.01), an AC 50 is found for 40 µM for 2,4-diamino-6-piperidinopyrimidine 3-oxide.

EXAMPLE 3

Dermal cream:

A dermal cream is prepared by mixing the following ingredients:

| 2,4-Diamino-6-piperidinopyrimidine 3-oxide | 0.5 g |
|---|---|
| Ceteareth 30 | 7 g |
| Glyceryl stearate | 2 g |
| Cetyl alcohol | 1.5 g |
| Polydimethylsiloxane | 1.5 g |
| Paraffin oil | 15 g |
| Pure glycerine codex | 20 g |
| Preservatives | qs |
| Demineralized water | qs 100 g |

EXAMPLE 4

Dermal lotion for spraying:

A dermal lotion for spraying is prepared by mixing the following ingredients:

| 2,4-Dipropylamino-6-dimethylaminopyrimidine 3-oxide | 0.025 g |
|---|---|
| Ethanol | 30 g |
| Demineralized water | qs 100 g |

EXAMPLE 5

Injectable solution:

A solution which can be injected intradermally is prepared by mixing the following ingredients:

| 2-Amino-4-propylamino-6-piperidinopyrimidine 3-oxide | 0.01 mg |
|---|---|
| Physiological saline (NaCl 9 g/H$_2$O qs 100 ml) | qs 11 ml |

What is claimed is:

1. A pharmaceutical or cosmetic composition which comprising a pharmaceutically or cosmetically acceptable amount of
   a) at least one pyrimidine derivative substituted at the 6th position that activates and/or stabilizes cyclooxygenase;
   b) one of the following:
      (I) a cyclooxygenase enzyme; or
      (ii) a cyclooxygenase enzyme and at least one cyclooxygenase substrate comprising a polyunsaturated fatty acid having at least 20 carbon atoms; and
   c) a pharmaceutically or cosmetically acceptable carrier and/or adjuvant.

2. The composition of claim 1, wherein said at least one pyrimidine derivative is a pyrimidine 3-oxide derivative substituted at the 6th position.

3. The composition of claim 1, wherein said pyrimidine derivative is selected from the group consisting of: 2,4-diamino-6-piperidinopyrimidine, 2,4-diamino-6-piperidinopyrimidine 3-oxide, 2,4-dipropylamino-6-dimethylaminopyrimidine 3-oxide, 2-amino-4-propylamino-6-piperidinopyrimidine 3-oxide, 2-methyl-4-amino-6-piperidinopyrimidine 3-oxide, 2,4-diamino-6-butyloxypyrimidine 3-oxide, and 2-amino-4-propylamino-6-dimethylaminopyrimidine 3-oxide.

4. The composition of claim 3, wherein said pyrimidine derivative is selected from the group consisting of: 2,4-diamino-6-piperidinopyrimidine 3-oxide, 2,4-dipropylamino-6-dimethylaminopyrimidine 3-oxide, and 2-amino-4-propylamino-6-piperidinopyrimidine 3-oxide.

5. The composition of claim 1, which comprises at least one cyclooxygenase substrate.

6. The composition according to claim 5, which comprises at least one pyrimidine 3-oxide derivative substituted at the 6th position.

7. The composition according to claim 6, wherein the pyrimidine derivative is selected from the group consisting of: 2,4-diamino-6-piperidinopyrimidine, 2,4-diamino-6-piperidinopyrimidine 3-oxide, 2,4-dipropylamino-6-dimethylaminopyrimidine 3-oxide, 2-amino-4-propylamino-6-piperidinopyrimidine 3-oxide, 2-methyl-4-amino-6-piperidinopyrimidine 3-oxide, 2,4-diamino-6-butyloxypyrimidine 3-oxide, and 2-amino-4-propylamino-6-dimethylaminopyrimidine 3-oxide.

8. The composition according to claim 7, wherein the pyrimidine derivative is selected from the group consisting of: 2,4-diamino-6-piperidinopyrimidine 3-oxide, 2,4-dipropylamino-6-dimethylaminopyrimidine 3-oxide, and 2-amino-4-propylamino-6-piperidinopyrimidine 3-oxide.

9. The composition of claim 1 or 5 wherein the cyclooxygenase substrate is arachidonic acid, dihomo-γ-linolenic acid or eicosatetraenoic acid.

10. The composition according to claim 1, wherein said cyclooxygenase is in purified form.

11. A method of treatment of a dermatological condition comprising administering an effective amount of a composition according to claim 1 to a person in need of such treatment.

12. The method according to claim 11, wherein said dermatological condition is selected from the group consisting of alopecia, solar erythema, pruritus, eczema, psoriasis, erythema nodosum, urticaria and systemic mastocytosis.

13. A method of treating wounds or epistaxis or changes to the skin associated with aging comprising administering a therapeutically effective amount of a composition according to claim 1.

14. The method of claim 12, which comprises the treatment of alopecia.

15. The method of claim 14, wherein the administered composition comprises a pyrimidine derivative selected from the group consisting of: 2,4-diamino-6-piperidinopyrimidine 3-oxide, 2,4-dipropylamino-6-dimethylaminopyrimidine 3-oxide and 2-amino-4-propylamino-6-piperidinopyrimidine 3-oxide.

16. The method of claim 11, wherein the composition is administered locally or systemically.

17. The method of claim 16, wherein systemic administration comprises parenteral, enteral or oral administration.

18. The method of claim 16, wherein local administration comprises direct application to the skin, scalp, nails or mucous membranes.

19. The composition of claim 1, which further comprises an adjuvant and/or a carrier selected from the group consisting of surface-active agents, emulsifying agents, gelling agents, thickening agents, oils, preservatives, hydrophilic active agents, lipophilic active agents, alkalinizing or acidifying agents, preservatives, antioxidants, solvents, perfumes, fillers, screening agents, bactericides, odor absorbers and coloring matter.

20. The composition of claim 1, which is in the form of a lotion, gel, emulsion or cream.

21. The composition of claim 19, wherein the amount of said adjuvant and/or a carrier range from 0.01% to 90% of the total weight of the composition.

22. The composition of claim 1, which is anhydrous.

23. The composition of claim 22, which comprises at least one solvent selected from the group consisting of $C_2$–$C_4$ lower alcohols, alkylene glycols, alkyl ethers of alkylene glycols or dialkylene glycols.

24. The composition of claim 1, wherein said fatty acid is arachidonic acid.

* * * * *